US008801630B2

(12) United States Patent
Yamatani et al.

(10) Patent No.: US 8,801,630 B2
(45) Date of Patent: Aug. 12, 2014

(54) METHOD OF TAKING OUT LIQUID PRESENT INSIDE SUBJECT THEREFROM

(75) Inventors: Ken Yamatani, Fuchu (JP); Kunihide Kaji, Hachioji (JP)

(73) Assignee: Olympus Medical Systems Corp., Tokyo (JP)

( * ) Notice: Subject to any disclaimer, the term of this patent is extended or adjusted under 35 U.S.C. 154(b) by 489 days.

(21) Appl. No.: 13/249,471

(22) Filed: Sep. 30, 2011

(65) Prior Publication Data

US 2013/0085414 A1  Apr. 4, 2013

(51) Int. Cl.
*A61B 5/00* (2006.01)

(52) U.S. Cl.
USPC .......................................................... 600/581

(58) Field of Classification Search
CPC ..................... A61B 10/0045; A61B 2217/005; A61M 1/0021; A61M 1/0023
USPC .................. 600/573, 576, 578, 581
See application file for complete search history.

(56) References Cited

U.S. PATENT DOCUMENTS

| | | | | |
|---|---|---|---|---|
| 4,773,430 | A | * | 9/1988 | Porath .......................... 600/581 |
| 4,799,925 | A | * | 1/1989 | Rosenblatt ..................... 604/181 |
| 4,854,322 | A | * | 8/1989 | Ash et al. ....................... 600/347 |
| 5,685,843 | A | * | 11/1997 | Enhorning ..................... 604/500 |
| 7,909,827 | B2 | * | 3/2011 | Reiley et al. ................... 606/79 |
| 8,251,945 | B2 | * | 8/2012 | Secrest et al. ................... 604/35 |
| 8,267,908 | B2 | * | 9/2012 | Coulthard ..................... 604/313 |
| 2007/0043351 | A1 | | 2/2007 | Fleischman et al. | |

FOREIGN PATENT DOCUMENTS

JP    10-024009    1/1998

OTHER PUBLICATIONS

International Publication No. WO 2006/065913 A1 English language abstract only dated Jun. 22, 2006.
International Publication No. WO 2007/037785 A1 English language abstract only dated Apr. 5, 2007.
International Publication No. WO 95/17849 A1 English language abstract only dated Jul. 6, 1995.
International Publication No. WO 96/04875 A1 English language abstract only dated Feb. 22, 1996.
International Publication No. WO 2006/058328 A2 English language abstract only dated Jun. 1, 2006.

* cited by examiner

*Primary Examiner* — Max Hindenburg
(74) *Attorney, Agent, or Firm* — Scully, Scott, Murphy & Presser, P.C.

(57) ABSTRACT

A method is provided to collect liquid, such as pancreatic juice water, and saline, from a body cavity of a subject. In the method, a tool is inserted through the body cavity to reach a target site in the body cavity. A body position of the subject is adjusted such that the wall surface of the body cavity including the target site intersects with a direction of gravitational force and the liquid present in the body cavity gathers on the wall surface intersecting with the direction of gravitational force. A recess is formed to be concaved on the wall surface in the direction of the gravitational force by making the tool press the wall surface of the body cavity. Therefore, the liquid present or discharged in the body cavity is accumulated in the recess. The liquid accumulated in the recess is taken out of the body of the subject.

11 Claims, 6 Drawing Sheets

METHOD OF TAKING OUT LIQUID PRESENT INSIDE SUBJECT THEREFROM

BACKGROUND OF THE INVENTION

1. Field of the Invention

The present invention relates to a method of taking out liquid present inside a subject therefrom, and in particular, the present invention relates to a method of taking out liquid inside a body cavity of a subject from the subject's body using a tool, such as a collecting tool, under endoscopic treatments with an endoscope inserted into the body cavity.

2. Description of the Related Art

Rapid advancements are being made in endoscopic examinations and treatments for diseases of the gall bladder and the pancreas, such as biliary tract cancer and pancreatic cancer, gallstones, and common bile duct stones. Compared to surgical treatments, endoscopic examinations and treatments are less invasive and less taxing on patients.

Endoscopic examinations are also useful in early detection of diseases such as cancer. Currently, as a method of early detection of cancer, secretion (a type of body fluid) and cells are collected from within the body of a subject, and the collected secretion and cells are examined. For example, if the pancreas is examined, this method involves collection of pancreatic juice. This method is known as sampling tube cytology or brush cytology performed under fluoroscopy.

In such sampling tube cytology and brush cytology, a collecting tool (treatment tool) is inserted into an inserting section of an endoscope that has been sent inside the pancreas under fluoroscopy and collects the pancreatic juice. The inside of the pancreas is cloudy as a result of an x-ray contrast agent administered in advance for fluoroscopy and suspended cells. Therefore, sampling tube cytology is performed after the inside of the pancreatic duct is flushed with saline and the cloudy fluid is drained. After flushing, the pancreatic juice that discharges from the inner wall of the pancreas is collected. In brush cytology, a brush used for collection is inserted into the pancreatic duct and swabs the pancreatic duct. The pancreatic juice is collected such as to be scraped off.

Specific methods that can be used in cytology, such as those described above, are described, for example, in JP-A-2008-523909 and JP-A-H09-507142. JP-A-2008-523909 describes a method in which a body fluid secreted after administration of a drug or a body fluid naturally secreted without administration of a drug is aspirated. JP-A-H09-507142 also describes a method in which a catheter is sent to a collection site through an endoscope and aspirates a body fluid.

SUMMARY

Hence, it is desired to take out liquids (body fluids and liquid substances) from the body of a subject in an efficient and fast manner.

According to an exemplary embodiment, there is provided a method of taking out liquid present in a body cavity of a subject from the body cavity outside the subject. This method includes a first step of inserting a tool through the body cavity of the subject to reach a target site in the body cavity, the tool being for pressing press a wall surface of the body cavity; a second step of adjusting a body position of the subject such that the wall surface of the body cavity including the target site intersects with a direction of gravitational force and the liquid present in the body cavity gathers on the wall surface intersecting with the direction of gravitational force; a third step of forming a recess concaved on the wall surface in the direction of the gravitational force by making the tool press the wall surface of the body cavity; a fourth step of accumulating the liquid present in the body cavity in the recess; and a fifth step of taking out, outside of the body of the subject, the liquid accumulated in the recess.

As a result of actively forming the recess in the wall surface (including the bottom section) of the body cavity, the liquid inside the body cavity can be dripped (accumulated) into the recess using the slope formed by the recess and its periphery. Hence, the liquid accumulated in the recess can be taken out from the body at once. In other words, when the liquid is a body fluid, the body fluid can be efficiently collected (obtained). When the liquid is a liquid substance, such as water or saline, the liquid substance can be efficiently collected. Therefore, the liquid can be collected efficiently in a shorter period of time.

DETAILED DESCRIPTION OF THE PREFERRED EMBODIMENTS

A preferred embodiment of a method of collecting liquid (liquid substances and body fluids) from inside of a subject, which is according to the present invention, will hereinafter be described with reference to the drawings.

The types of liquid to be collected in the present invention include all types of liquid present inside of body cavities of a subject, which can be collected using a collecting tool, under endoscopic treatments or examinations with an endoscope. The liquid includes liquid substances that have been brought into the body from outside, such as water and saline used in examinations and surgeries, and body fluids originating from within the body for examination and the like. The body fluids include pancreatic juice, bile, gastric juice, intestinal juice, and the like. The manner in which these fluids are present can be classified into accumulated fluid, secreted fluid, and the like. Blood which bleeds from blood vessels is also liquid to be collected by the collecting method according to the present embodiment.

In the present embodiment, the procedure of "taking out" liquid from inside a subject means an action that collects (or obtains) liquid substances that have been brought into the body from outside and/or target body juices present in the body.

A method of collecting liquid according to the present embodiment will be described giving as an example an instance in which duodenal juice from the pancreatic duct, flowing out of the wall of the duodenum (lumen) of the subject, is collected (that is, the collecting method is used to "obtain" the duodenal juice or "taking out" the duodenal juice outside the body. Incidentally the duodenal juice is liquid secreted from mucous membrane.

Figure 1:
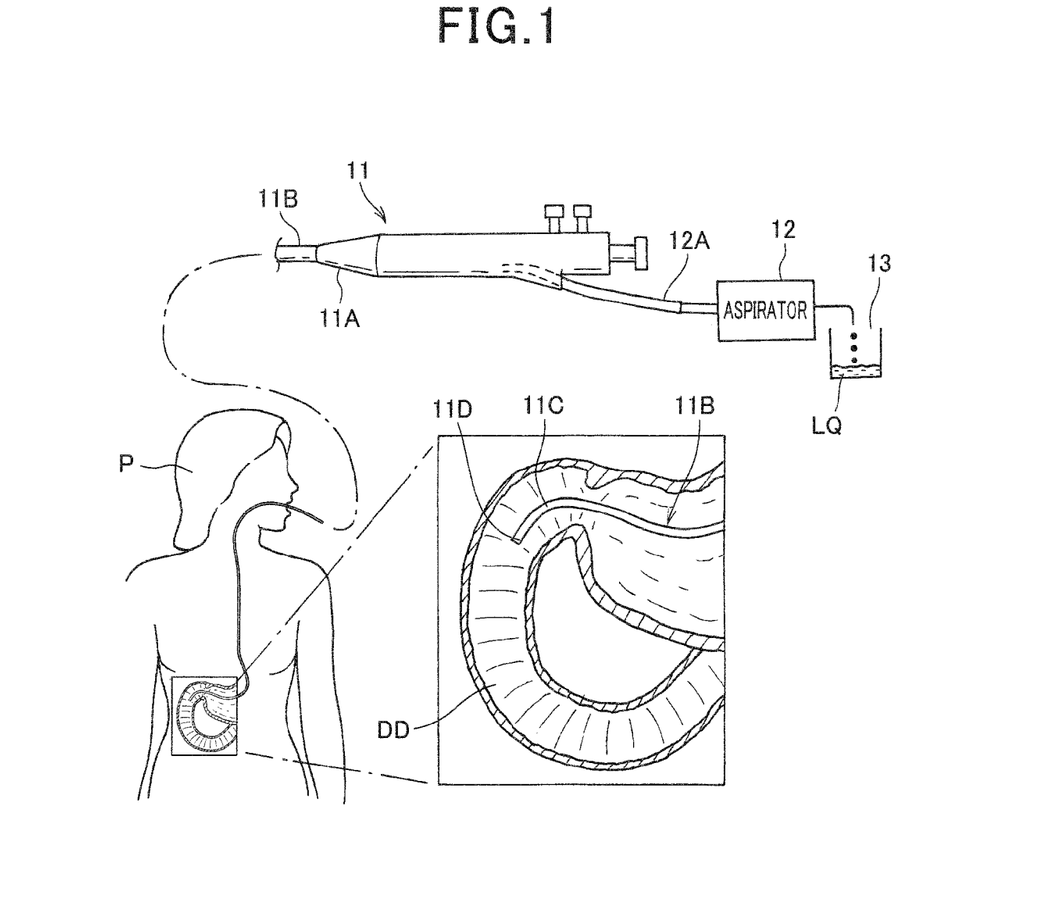
FIG. 1 is a configuration diagram explaining a system for collecting liquid in a body cavity of a subject, which practices an embodiment of a liquid collecting method according to the present invention.

As shown in FIG. 1, the method of collecting liquid is performed using a complex system including a flexible endoscope 11 and an aspirator 12. The endoscope 11 is orally inserted into a lumen of a subject (patient). The aspirator 12 serves as a collecting tool working in cooperation with the endoscope 11.

The flexible endoscope 11 has a hand operating section 11A and a flexible, narrow tube-shaped inserting section 11B that is coupled with the hand operating section 11A. The inserting section 11B has a tip rigid section 11D integrally formed in a tip portion of the inserting section 11B with a curved section 11C therebetween. A light, a charged-coupled device (CCD) camera, and the like (not shown) are mounted in the tip rigid section 11D. Wiring for transmitting power supply to the light, the CCD camera, and the like, and image signals passes through the inserting section 11B to the hand operating section 11A. The hand operating section 11A and the tip rigid section 11D are also connected by various channels through the inserting section 11B. The channels include a treatment tool channel.

The treatment tool channel connects an opening on the side surface of the hand operating section 11A and an opening on the front surface of the tip rigid section 11D. An aspiration catheter 12A of the aspirator 12 is inserted into the treatment tool channel. This aspiration catheter 12A functions as part of the collecting tool. The aspiration catheter 12A is a flexible tube that is narrower than the inner diameter of the treatment tool channel. A tip portion 12AP of a predetermined area in an axial direction of the aspiration catheter 12A including a tip section 12AT has a hole HL. The hole HL is formed in the tip section 12AT that is formed to be slightly firm, and is appropriately sized. The duodenal juice serving as the liquid can be aspirated (sucked out) by the aspirator 12 through the hole HL.

The example in which the duodenal juice is collected according to the present embodiment will be described in detail with reference to FIG. 2 and FIG. 3.

Figure 2:
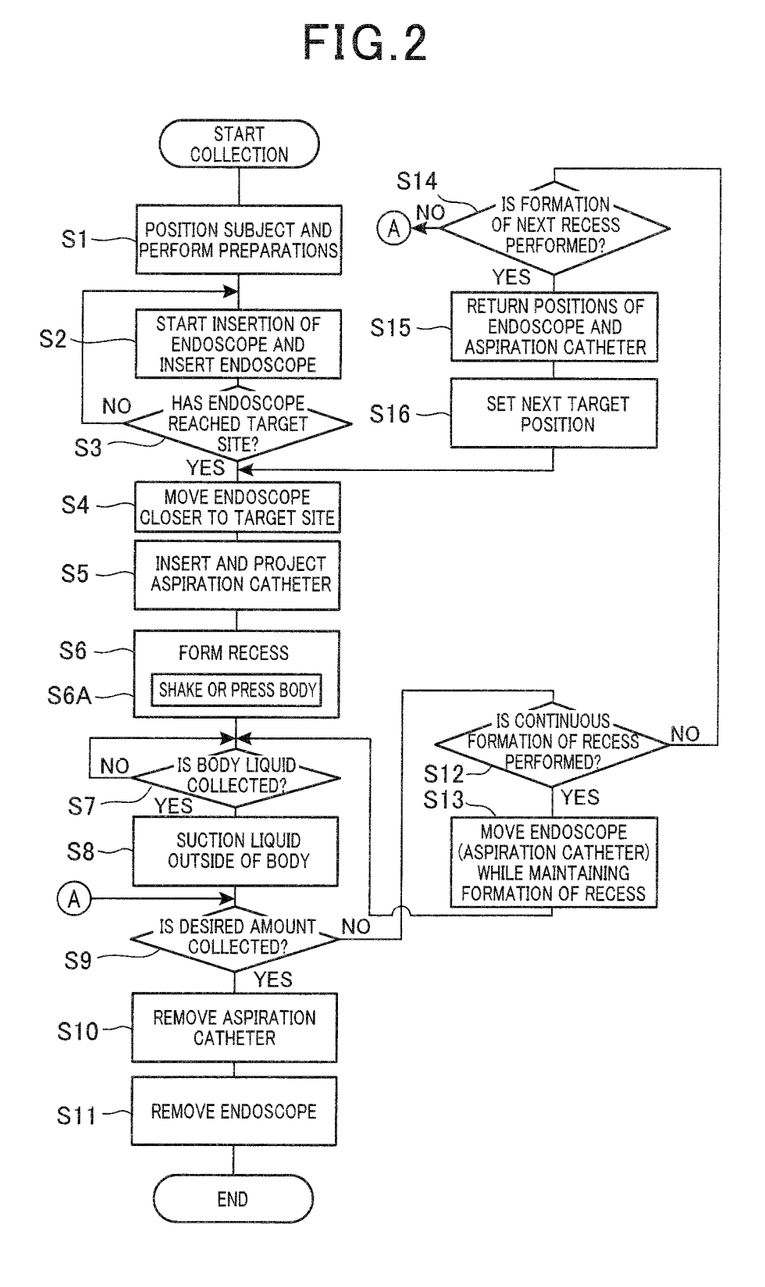
FIG. 2 is a flowchart explaining operation procedures for collecting the liquid, which is according to the embodiment.

First, various preparations for duodenal juice collection are performed while a subject P is lying on a patient bed (Step S1 in FIG. 2). The preparation procedure includes, for example: the subject P entering the treatment room; a process for externally observing the subject P using an observation instrument (such as X-ray computed tomography [X-ray CT] or magnetic resonance imaging [MRI]); the subject P being secured in a desired position on the patient bed; and a drug for inducing secretion of the duodenal juice being administered in advance. Therefore, the subject P is placed on the patient bed such that a set target site is facing downwards, namely in the direction of gravitational force. The target site may be set and oriented in a dedicated room in which the observation instrument is installed.

When the preparations are completed, the operator orally inserts the inserting section 11B of the flexible endoscope 11 into the subject P, under observation using the observation instrument (Step S2). As shown in FIG. 1, the inserting section 11B passes through the stomach ST and the pylorus, and enters the duodenum JD. The duodenum JD includes the superior part following the pylorus, the flexure, the descending part, and the duodenojejunal flexure.

Figure 3:
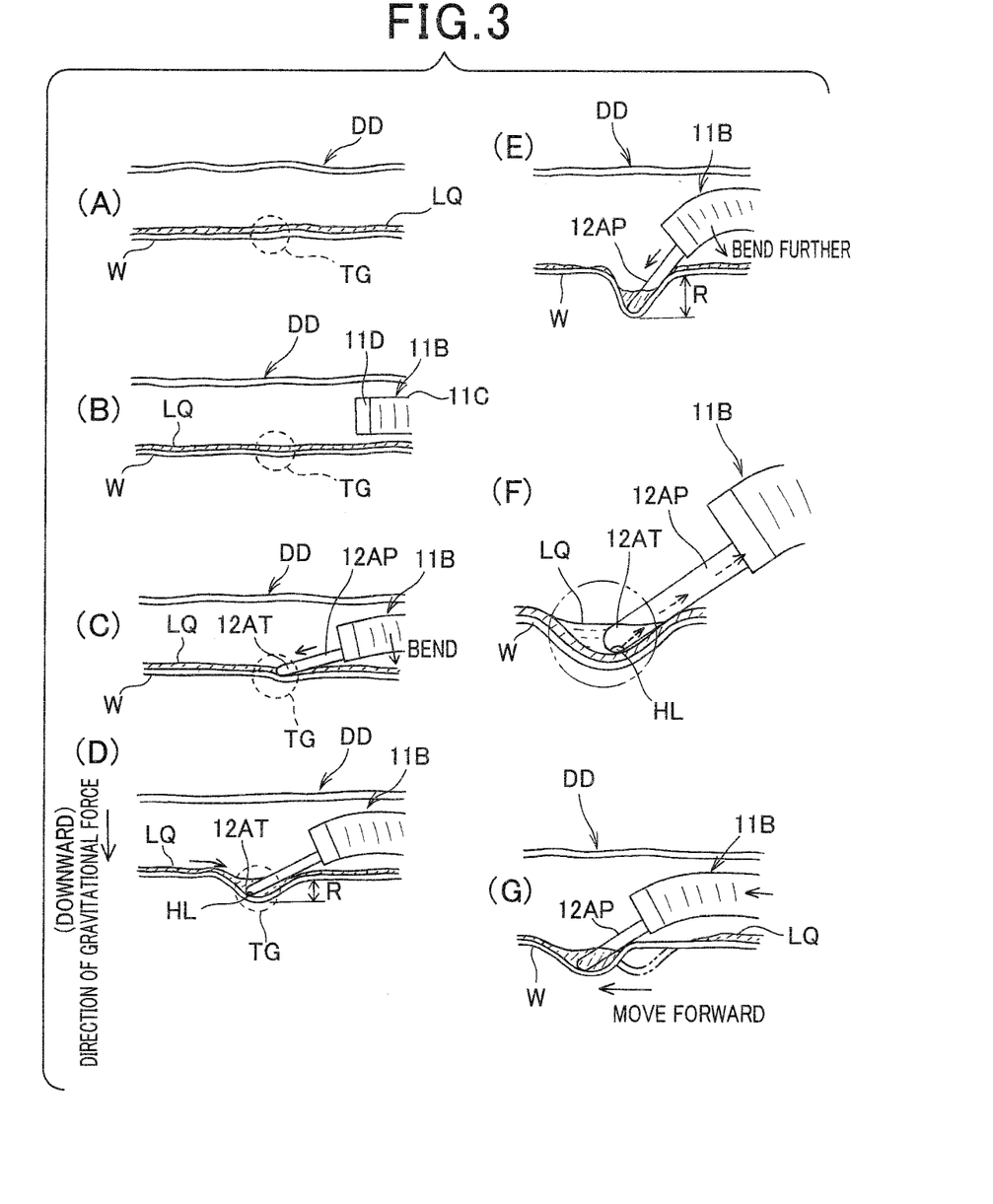
FIG. 3 is an explanatory diagram explaining some of the operation procedures for collecting duodenal juice serving as a liquid.

The operator judges whether or not the inserting section 11B of the endoscope 11 has passed through the superior part and reached the vicinity of a target site TG that is an inner wall near the opening of a papillary portion (major duodenal papilla) PA (see FIG. 4) of the flexure, while viewing an endoscopic image (Step S3; see FIG. 3(A)). The target site TG is an area where the duodenal juice present or being secreted in the vicinity on the inner wall of the duodenum is collected. The target site TG is preferably as close to the papillary portion as possible.

The operator moves the tip section of the inserting section 11B closer to the target site TG while observing the endoscopic image (Step S4; see FIG. 3(B)).

When judged that the tip section of the inserting section 11B is sufficiently near the target site TG, the operator sends the collecting tool 12 through the treatment tool channel of the inserting section 11B such that the tip portion 12AP of the aspiration catheter 12A of the aspirator 12 projects from the tip of the inserting section 11B. In addition, the operator bends the curved section 11C of the endoscope 11 slightly downwards and directs the tip rigid section 11D such as to face downwards (Step S5; see FIG. 3(C)).

Then the operator sets the curve angle of the curved section 11C of the endoscope 11 to a deeper angle, thereby deepening the downward angle of the tip rigid section 11D (Step S6). As a result, as shown in FIG. 3(D), the tip section 12AT of the collecting tool 12 presses a wall surface W of the duodenum in a downward direction (direction of gravitational force). The wall surface W is composed of elastic layers of muscle. Hence, a recess R that recesses in the direction of gravitational force is formed on the wall surface W.

As a result, the recess R becomes the lowest portion in terms of the plane of the wall surface W, and its peripheral surface also faces downwards at an angle by being pulled by the recess R. Therefore, as a result of the state in which the recess R is formed being maintained for a desired amount of time (several seconds or several tens of seconds), the duodenal juice LQ present within and around the recess R and newly secreted from the wall surface is accumulated.

The timing at which the recess R is formed may be before the duodenal juice is present, or after a certain amount or a sufficient amount of duodenal juice has been secreted and accumulated on the wall surface W.

To promote accumulation of the duodenal juice LQ in the recess R, the operator may press the abdominal section of the patient (subject P), or the operator or the patient himself may shake the patient's body (Step S6A).

The depth of the recess R and the amount of time over which the recess R is maintained depends on judgment by the operator. The recess R shown in FIG. 3(E) is deeper than that shown in FIG. 3(D). Control of the depth of the recess R is determined by the extent of curving of the curved section 11C of the endoscope 11 and how far the tip portion 12AP of the aspiration catheter 12A projects from the tip (tip rigid section) of the inserting section 11B of the endoscope 11.

The tip section 12AT of the collecting tool 12 is rounded, thereby preventing damage to the wall surface W of the duodenum caused by the wall surface W being pressed.

Figure 4:
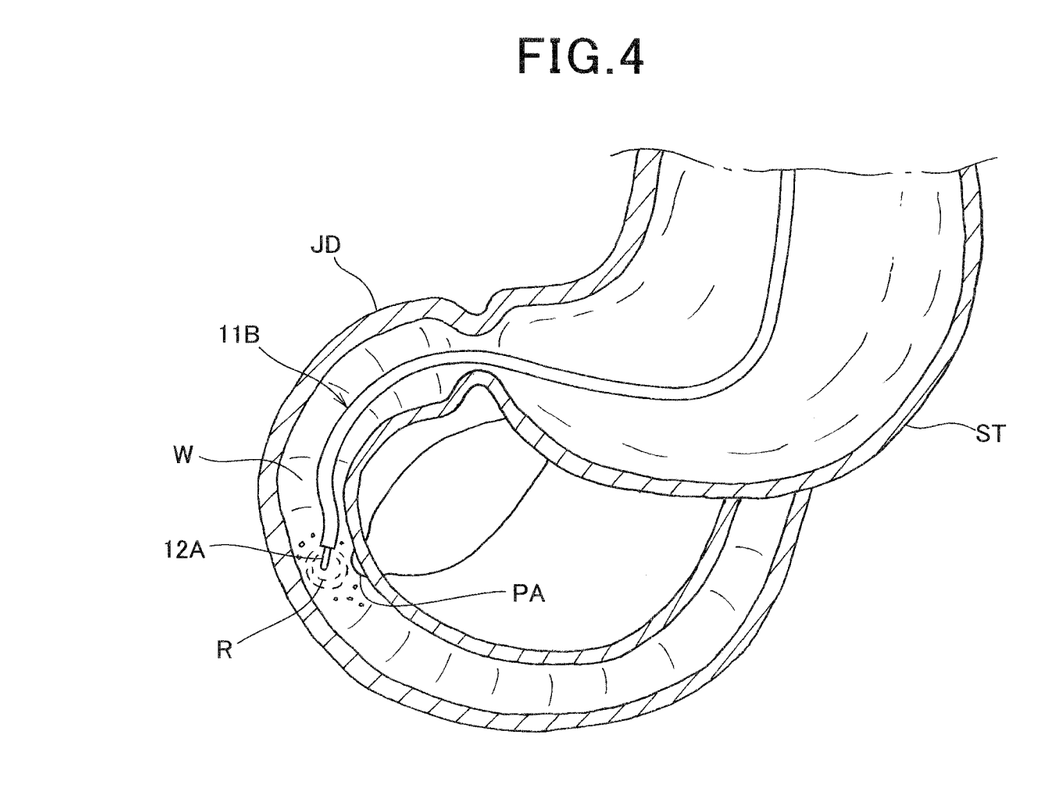
FIG. 4 is an explanatory diagram explaining the collection of duodenal juice near a papillary portion of the duodenum.

Then the operator judges whether a sufficient amount of duodenal juice LQ has been accumulated or the duodenal juice LQ should be immediately collected from the current recess R because of insufficient accumulation while monitoring the amount of duodenal juice LQ accumulated in the recess R using an endoscopic image. In other words, the operator judges whether or not the timing for collecting the duodenal juice LQ has been reached (Step S7). When judged YES, the aspirator 12 is driven, and the duodenal juice LQ is aspirated (sucked out) through the hole HL in the tip section 12AT of the aspiration catheter 12A (Step S8). As a result, as indicated by the dotted lines in FIG. 3(F), the accumulated duodenal juice LQ is sucked out through the hole HL, passes through the hole HL, the aspiration catheter 12A, and the aspirator 12, and is collected in a container 13 set in the aspirator 12. As a result, the duodenal juice LQ is collected outside of the body. In other words, as shown in FIG. 4, the duodenal juice LQ accumulated in the recess R formed near the papillary portion PA on the wall surface W of the duodenum JD can be collected by the aspiration catheter 12A.

The operator then judges whether or not the amount of duodenal juice LQ collected in the container 13 is sufficient for testing (Step S9). When judged that a sufficient amount has been secured, the aspiration catheter 12A and the inserting section 11B of the endoscope 11 are removed, and collection of the duodenal juice is completed (Step S10 and Step S11).

However, when the amount of collected duodenal juice LQ is still insufficient, two methods can be used to form a next recess.

In a first method, the currently formed recess R is moved by being dragged slowly and continually or intermittently, in the front, back, left, right, and diagonal directions on the wall surface W (Step S12). When the operator selects this movement method, the operator moves the inserting section 11B in the desired front, back, left, right, diagonal direction while maintaining the position of the tip end section of the endoscope 11, or in other words, the curved section 11C (Step S13). At this time, the depth of the recess R being moved in the front, back, left, right, diagonal direction can be adjusted by adjusting the amount by which the tip portion 12AP of the aspiration catheter 12A projects from the tip of the endoscope 11. In FIG. 3(G), an instance in which the recess R is continuously formed in the forward direction is shown. Because the wall surface W is elastic, the previously formed recess R immediately disappears with the movement of the aspiration catheter 12A, or in other words, the inserting section 11B of the endoscope 11. As a result, by waiting for an appropriate amount of time at the position of each recess R during the process of continuously forming the recess R, the duodenal juice LQ can be collected. This method is suitable for collecting the duodenal juice LQ while tracking the duodenal juice LQ present on the wall surface W while observing the endoscopic image.

When judged NO at Step S10 in FIG. 2, the operator performs a second method indicated by Step S12 and Step S13. The second method is performed when the recess R is formed in another location (Step S14). In this instance, at least the curve angle of the curved section 11C of the endoscope 11 is lessened or returned to a horizontal state (Step S15). As a result, the tip section 12AT of the aspiration catheter 12A moves away from the recess R that had been formed, realizing a state shown in FIG. 3 (B) or FIG. 3 (C).

Then, the operator searches for a next target site TG while viewing an endoscopic image (Step S16). When the next target site TG is determined as a result, the operator performs the process at above-described Step 54. As a result, the duodenal juice LQ can be collected in a manner similar to that described above, at the new target site TG.

The above-described first method and second method may also both be performed in an appropriate order.

When the collection operation according to the present embodiment is performed as described above, the recess R that recesses in the direction of gravitational force can be actively formed on the wall surface W of the body cavity of the subject. Therefore, the duodenal juice LQ present in the recess R and its the vicinity can be quickly and efficiently collected in the recess R using gravitational force. The duodenal juice LQ being discharged from the area is also accumulated in the recess R. Therefore, unlike a conventional method in which the duodenal juice present on the wall surface of the duodenum is accumulated by the aspiration while searching for the duodenal juice while observing the endoscopic image, the duodenal juice LQ can be actively accumulated from a greater area using the slope of the recess R. The accumulated duodenal juice LQ can be sucked out of the body at once when a certain amount has been accumulated or a certain amount of time has elapsed. As a result, the time required to aspirate the duodenal juice out of the body, or in other words, to collect the duodenal juice can be significantly shortened. For example, a conventional collection time of 30 minutes can be shortened to several minutes.

In addition, as shown in FIG. 3(G), the inserting section 11B of the endoscope 11, or in other words, the tip portion 12AP of the aspiration catheter 12A can be continuously moved in a state in which the recess R is formed. As a result, accumulation and aspiration of the duodenal juice LQ taking advantage of the slope of the continuous recess R can be continuously performed, albeit at a slow speed, while following the areas in which the duodenal juice LQ is present. As a result, collection efficiency can be further improved.

Accordingly, in the collection method according to the present embodiment, the duodenal juice in the duodenum can be quickly and efficiently collected. Compared to conventional technology, the burden of examination placed on the subject and the burden of operation placed on the operator can be significantly reduced.

The liquid to which the method of collection according to the present invention is not only the pancreatic juice but also various types of liquid (accumulated fluids) present on the wall surface of a body cavity of the subject, such as bile, stomach juice, and intestinal juice, and body fluids (secreted fluids) being secreted from the wall surface. Furthermore, the present invention also includes methods of recovering fluids brought into the body from outside, such as water and saline, used for examinations and surgeries under an endoscope.

Other examples of methods of collecting liquid will be described with reference to FIG. 5 to FIG. 7.

Figure 5:
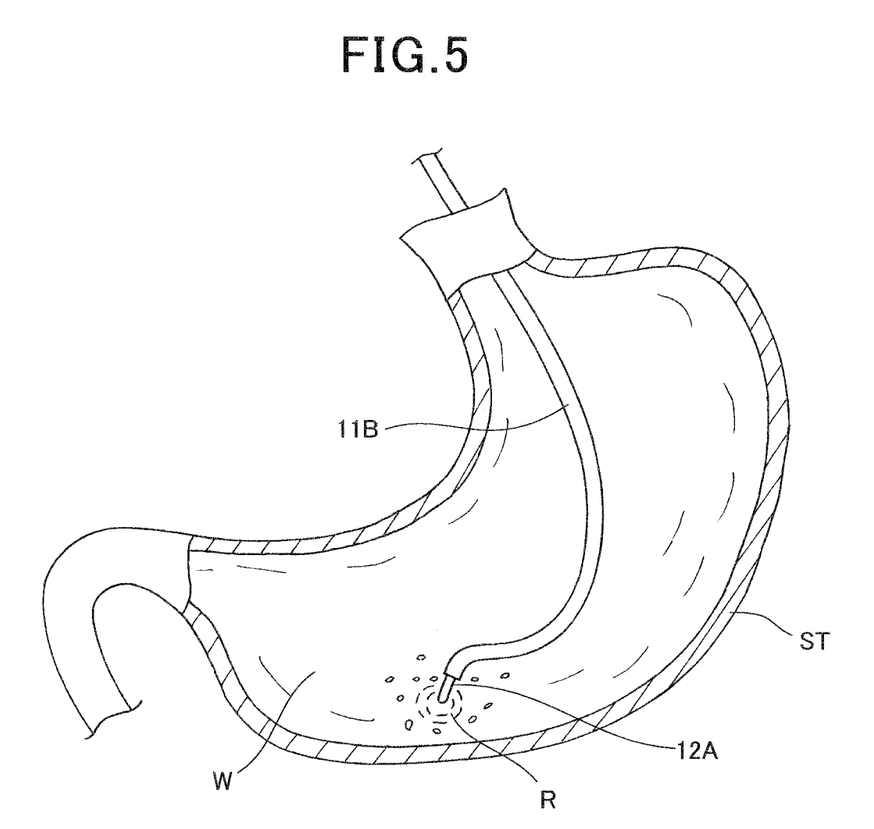
FIG. 5 to FIG. 7 are explanatory diagrams each explaining other examples of the method for collecting (taking out) liquid, which is according to the present invention.

FIG. 5 shows an example in which water for flushing and gastric acid resulting from hyperacidity are collected from the stomach ST of the subject using an upper GI endoscope 11 and the aspirator 12. The recess R is formed on the wall surface of the stomach ST in a manner similar to that described above. Water and gastric acid accumulated in the recess R are collected using the aspiration catheter 12A.

Figure 6:
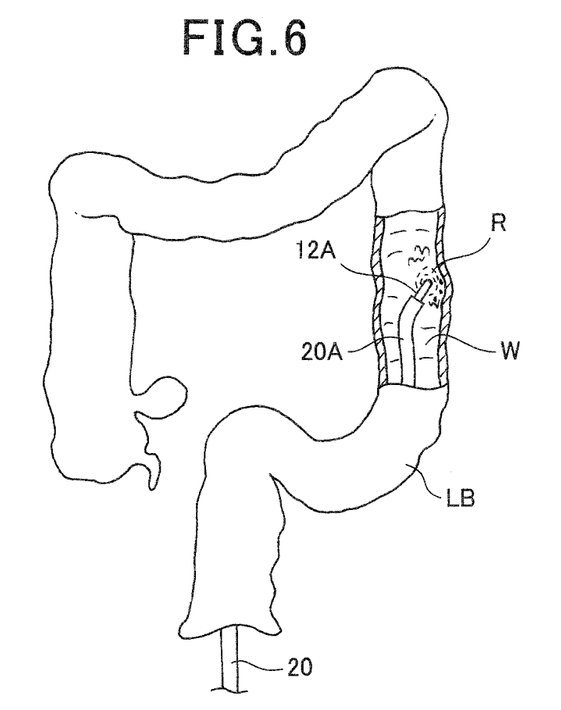

FIG. 6 shows an example in which water sent from the large bowel LB to the endoscope is collected using a lower GI endoscope 20 and the aspirator 12. The recess R is formed on the wall surface of the large bowel LB in a manner similar to that described above. Water accumulated in the recess R is collected using the aspiration catheter 12A that has been inserted into an inserting section 20A of the lower GI endoscope 20.

Figure 7:
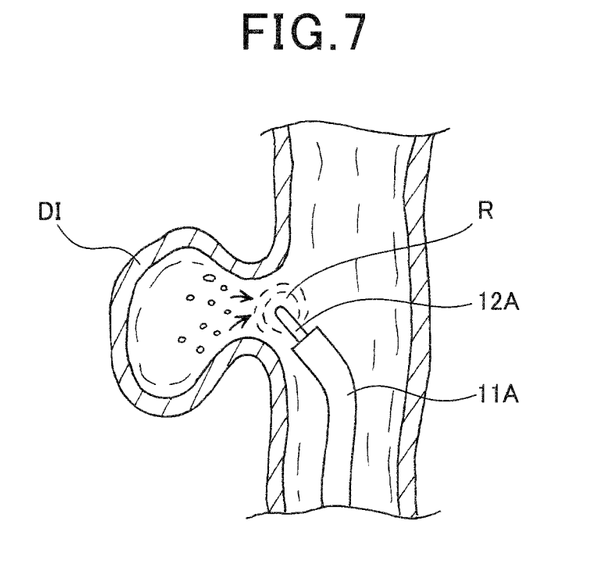

FIG. 7 shows an example in which fluid filled or discharged in a cyst or a diverticulum (collectively given the reference number DI) in the subject is collected using the lower GI endoscope 20 and the aspirator 12. The diverticulum is a portion locally extended from an inner cavity and which are observed on organs including the esophagus, the small bowel, and the large bowel. There may be accumulated liquid in the diverticulum. A typical cyst is a pancreato-cyst, and, similarly to the diverticulum, the cyst may contain liquid.

In such cases, the liquid may be discharged from the diverticulum or the cyst by itself. If necessary, water is intentionally supplied into the cyst in order to discharge the liquid forcibly from the cyst. A recess R is formed around the diverticulum or the cyst or on the bowel wall therearound in the same manner described above, so that the discharged liquid is made to accumulate in the recess R and then sucked out. Similarly to the foregoing, the recess R can also be formed on the bowel wall prior to discharge of the liquid into the bowel.

In all of the methods of collecting the liquid shown in FIG. 5 to FIG. 7, the body position of the subject is adjusted such that the bottom portion of the recess R is positioned downward in the direction of gravitational force. As a result, the fluid can be efficiently accumulated in the recess R through active use of gravity. Therefore, operations and advantages equivalent to the above-described embodiment can be achieved by any of the methods of collecting the liquid.

The method of colleting the liquid according to the present invention is not limited to a method of taking out the liquid through a natural opening of the subject. A method in which the collecting tool for the collection is inserted into the body transdermally is also possible.

Further, differently from the foregoing embodiments, the liquid can be collected by methods other than the aspiration.

In addition, the present invention is not limited to the configurations according to the above-described embodiment and modifications thereof. Other suitable embodiments are possible through combination with conventionally known configurations, without departing from the scope of the invention recited in the scope of claims.

What is claimed is:

1. A method of taking out liquid present in a body cavity of a subject from the body cavity to an outside of the subject, the method comprising:
   a first step of inserting a tool through the body cavity of the subject to reach a target site in the body cavity, the tool pressing a wall surface of the body cavity;
   a second step of adjusting a body position of the subject such that the wall surface of the body cavity including the target site intersects with a direction of gravitational force and the liquid present in the body cavity gathers on the wall surface intersecting with the direction of gravitational force;
   a third step of forming a recess concaved on the wall surface in the direction of the gravitational force by making the tool press the wall surface of the body cavity;
   a fourth step of accumulating the liquid present in the body cavity in the recess; and
   a fifth step of taking out, outside of the body of the subject, the liquid accumulated in the recess.

2. The method of claim 1, wherein the fourth step includes a step of externally shaking the body during accumulation of the liquid.

3. The method of claim 2, wherein the tool is a collecting tool which collects the liquid from the recess.

4. The method of claim 3, wherein the collecting tool is an aspiration tool which aspirates the liquid outside the subject.

5. The method of claim 1, wherein the tool is guided to the target site by making the tool advance in along a long-axis member having a curved section at a tip thereof.

6. The method of claim 5, wherein the long-axis member is an endoscope with a channel, and
   the tool is guided to the target site along the channel of the endoscope.

7. The method of claim 3, wherein the third step includes
   a step of projecting a tip portion of the collecting tool from a tip of an inserting section of an endoscope and
   a step of curving a curved section of the endoscope towards the wall surface side at the target site in a state in which the tip portion of the collecting tool is projecting from the tip of a channel of an inserting section of the endoscope, the inserting section having a tip rigid section adjacently connected to the curved section.

8. The method of claim 3, wherein the fourth step is a step requiring wait-time that is either waiting in a state where formation of the recess is maintained until a desired amount of the liquid is accumulated in the recess, or waiting for a certain amount of time in a state in which formation of the recess is maintained.

9. The method of claim 7, wherein the third step is a step of continuously forming the recess by continuously moving the inserting section of the endoscope while maintaining the state in which the recess is formed.

10. The method of claim 3, wherein the collecting tool is inserted into a channel of an inserting section of a flexible endoscope inserted into the body cavity of the subject.

11. The method of claim 3, wherein the liquid taken out by the collecting tool is a body fluid present inside of the body of the subject or a liquid substance brought into the body from outside for surgery or examination.

* * * * *